United States Patent
Zhang et al.

(10) Patent No.: US 10,287,257 B2
(45) Date of Patent: *May 14, 2019

(54) LINKER MOLECULE FOR MULTIPLEX RECOGNITION BY ATOMIC FORCE MICROSCOPY (AFM)

(71) Applicant: Arizona Board of Regents on behalf of Arizona State University, Scottsdale, AZ (US)

(72) Inventors: Peiming Zhang, Gilbert, AZ (US); Stuart Lindsay, Phoenix, AZ (US); Saikat Manna, Tempe, AZ (US); Subhadip Senapati, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/308,517

(22) PCT Filed: May 7, 2015

(86) PCT No.: PCT/US2015/029746
§ 371 (c)(1),
(2) Date: Nov. 2, 2016

(87) PCT Pub. No.: WO2015/171930
PCT Pub. Date: Nov. 12, 2015

(65) Prior Publication Data
US 2017/0137389 A1 May 18, 2017

Related U.S. Application Data

(60) Provisional application No. 61/989,874, filed on May 7, 2014.

(51) Int. Cl.
| | | |
|---|---|---|
| C07D 249/04 | (2006.01) | |
| C07D 249/06 | (2006.01) | |
| C07D 491/052 | (2006.01) | |
| C07D 487/04 | (2006.01) | |
| C07C 247/04 | (2006.01) | |
| C07K 14/00 | (2006.01) | |
| C12N 15/115 | (2010.01) | |

(52) U.S. Cl.
CPC .......... *C07D 249/06* (2013.01); *C07C 247/04* (2013.01); *C07D 249/04* (2013.01); *C07D 487/04* (2013.01); *C07D 491/052* (2013.01); *C07K 14/001* (2013.01); *C12N 15/115* (2013.01); *C12N 2310/16* (2013.01); *C12N 2310/3517* (2013.01)

(58) Field of Classification Search
None
See application file for complete search history.

(56) References Cited

U.S. PATENT DOCUMENTS

| | | |
|---|---|---|
| 8,628,649 B2 | 1/2014 | Lindsay et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,395,352 B2 | 7/2016 | Lindsay et al. |
| 9,593,372 B2 | 3/2017 | Lindsay et al. |
| 2013/0302901 A1 | 11/2013 | Lindsay et al. |
| 2015/0010935 A1 | 1/2015 | Lindsay et al. |
| 2015/0142327 A1 | 5/2015 | Ashcroft et al. |
| 2015/0144506 A1 | 5/2015 | Lindsay et al. |
| 2016/0018384 A1 | 1/2016 | Lindsay et al. |
| 2016/0025702 A1 | 1/2016 | Lindsay et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0258925 A1 | 9/2016 | Gyarfas et al. |
| 2016/0280723 A1 | 9/2016 | Zhang et al. |
| 2017/0003245 A1 | 1/2017 | Lindsay et al. |
| 2017/0016852 A1 | 1/2017 | Lindsay et al. |
| 2017/0038369 A1 | 2/2017 | Lindsay et al. |
| 2017/0067902 A1 | 3/2017 | Zhang et al. |
| 2017/0204066 A1 | 7/2017 | Lindsay et al. |

FOREIGN PATENT DOCUMENTS

WO  WO 15/126963  *  2/2015  ............. C07C 43/00

OTHER PUBLICATIONS

STN Registry Database entry for CAS RN 1257866-73-1, Entry date Dec. 29, 2010, Accessed Feb. 26, 2018.*
STN Registry database entry for CAS RN 1312992-95-2, Entered STN Jul. 19, 2011, Accessed Oct. 3, 2018.*
Pubchem Substance Summary for Pubchem 53872374, deposited on Dec. 4, 2011, 1 page.
Senapati, et al. Application of Catalyst-free Click Reactions in Attaching Affinity Molecules to Tips of Atomic Force Microscopy for Detection of Protein Biomarkers in LANGMUIR, 2013, vol. 29, pp. 1-22.
Pubchem Substance Summary for Pubchem 24180240 Deposited on Feb. 26, 2006, 1 page.

(Continued)

*Primary Examiner* — Alicia L Otton
(74) *Attorney, Agent, or Firm* — Schwabe, Williamson & Wyatt, P.C.

(57) ABSTRACT

Some of the embodiments of the present disclosure relate to a compound of the formula, and methods of preparing and using same.

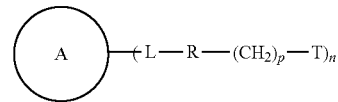

5 Claims, 2 Drawing Sheets
Specification includes a Sequence Listing.

(56) References Cited

OTHER PUBLICATIONS

Craig et al. "Effect of Linker and Spacer on the Design of a Fibronectin-Mimetic Peptide Evaluated via Cell Studies and AFM Adhesion Forces" Langmuir, 2008, 24(18), pp. 10282-10292 (Publication Date (Web): Aug. 12, 2008).

Hong et al. "Analysis and Optimization of Copper-Catalyzed Azide-Alkyne Cycloaddition for Bioconjugation" Angewandte Chemie International Edition, vol. 48, Issue 52, Dec. 21, 2009, pp. 9879-9883.

* cited by examiner

Topography (2*2 μm)

Recognition (for both proteins)

RGD blocked (recognition for Thrombin)

Both RGD and thrombin aptamer blocked (no recognition)

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Artificial polynucleotide

<400> SEQUENCE: 1
ggttggtgtg gttgg                    15

<210> SEQ ID NO 2

```
<211> LENGTH: 5
<212> TYPE: PRT
<213> ORGANISM: Artificial Sequence
<220> FEATURE:
<223> OTHER INFORMATION: Artificial polypeptide

<400> SEQUENCE: 2

Arg Gly Asp Phe Lys
1               5

<210> SEQ ID NO 3
<211> LENGTH: 23
<212> TYPE: PRT
<213> ORGANISM: Artificial Sequence
<220> FEATURE:
<223> OTHER INFORMATION: Artificial polypeptide

<400> SEQUENCE: 3

Lys Ser Ser Pro His Ser Arg Asn Ser Gly Ser Gly Ser Gly
1               5                   10                  15

Ser Gly Arg Gly Asp Ser Pro
            20
```

LINKER MOLECULE FOR MULTIPLEX RECOGNITION BY ATOMIC FORCE MICROSCOPY (AFM)

CROSS REFERENCE TO RELATED APPLICATIONS

This application is a U.S. national phase of PCT/US2015/029746, filed May 7, 2015, and claims priority to U.S. Provisional Application No. 61/989,874 titled "LINKER MOLECULE FOR MULTIPLEX RECOGNITION BY ATOMIC FORCE MICROCOSPY (AFM)", filed May 7, 2014, the entire disclosures of which are incorporated herein by reference.

STATEMENT OF GOVERNMENT SUPPORT

This invention was made with government support under R01 HG006323 awarded by the National Institutes of Health. The government has certain rights in the invention.

INCORPORATION BY REFERENCE OF SEQUENCE LISTING

The contents of the text file named "ARIZ-022-N01US_SEQ_LISTING.txt", which was created on Jun. 14, 2017 and is 1.08 KB in size, are hereby incorporated by reference in their entireties.

SUMMARY OF THE EMBODIMENTS

Embodiments of the present disclosure relate to a compound of the following formula:

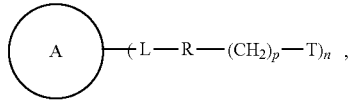

wherein each of

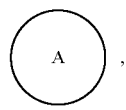

L, R, T, p, and n is as defined herein below.

Some embodiments of the present disclosure also relate to methods of conjugating some of the compound embodiments of the present disclosure, such as a compound of the formula shown above, with a target compound selected from the group consisting of a polypeptide, an oligonucleotide, an aptamer, and an antibody.

Some embodiments of the present disclosure also relate to methods of using some of the compound embodiments of the present disclosure, such as a compound of the formula shown above, in the detection of a compound of interest (e.g., a protein, an antibody, or a gene) with a detection device, such as a fluorescence microscope or an atomic force microscope.

Some embodiments of the present disclosure also relate to methods of using the compound embodiments of the present disclosure, such as a compound of the formula shown above, to deliver a compound of interest (e.g., a protein, an antibody, or a gene) to biological targets.

DETAILED DESCRIPTION OF SOME OF THE EMBODIMENTS

Figure 1:
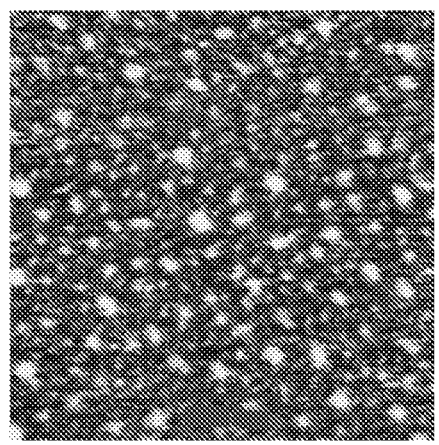
FIG. 1: Images of thrombin and integrin proteins recognized with an AFM tip functionalized with an anti-Thrombin aptamer and a cyclo-RGD through a three arm linker.
Figure 1:
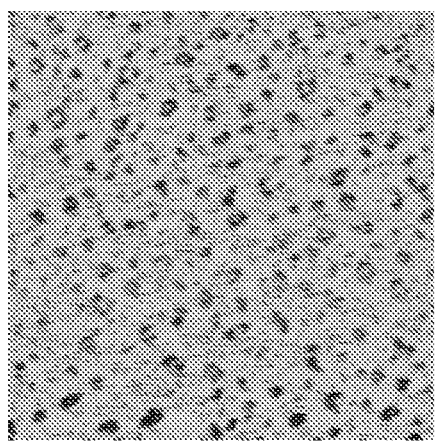
Figure 1:
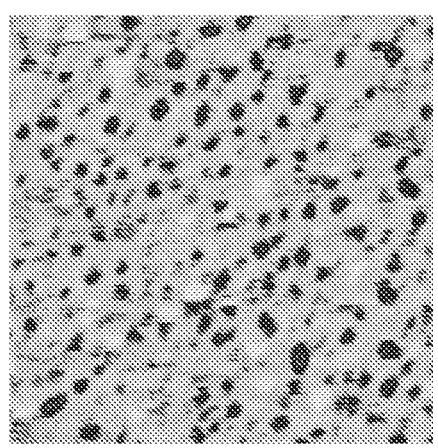
Figure 1:
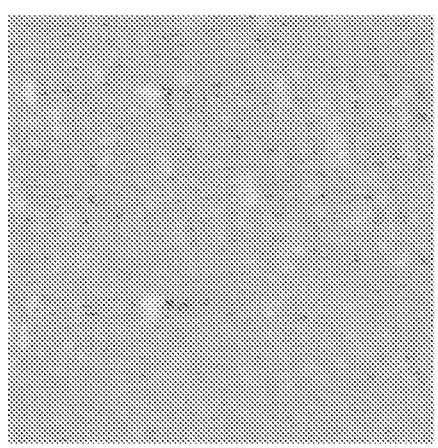

Some of the embodiments of the present disclosure relate to a compound of the following formula:

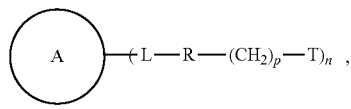

wherein:

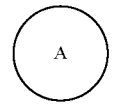

is a central unit with a plurality of available attachment points;
each L is independently a linker;
each R is independently a repeating unit;
each T is independently a reactive group;
each p is independently 0, 1, or 2; and
n is 2, 3, 4, 5, 6, 7, 8, or 9.

In one embodiment,

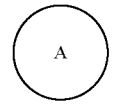

is phenyl or a $C_3$-$C_{12}$ carbocycle.

In one embodiment,

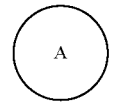

is phenyl. In a further embodiment, each L is

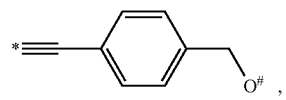

wherein * denotes the position that is linked to

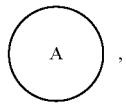

and # denotes the position that is linked to R. In a further embodiment, each R is independently

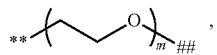

wherein each m is independently 1, 2, 3, 4, 5, 6, 7, 8, 9, 10, 11, 12, 13, 14, 15, 16, 17, 18, 19, 20, 21, 22, 23, or 24; **denotes the position that is linked to L; and ## denotes the position that is linked to T. In a further embodiment, each m is independently 6, 7, 8, 9, 10, 11, or 12. In a further embodiment, each R is

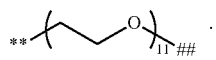

In a further embodiment, each T is independently a reactive group selected from the group consisting of $ONH_2$, SH, $NH_2$, alkyne, alkene, vinyl sulfone, maleimide, carboxylic acids, aldehyde, ketone, $N_3$. In a further embodiment, each T is $N_3$.

In another embodiment,

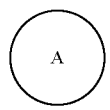

is a $C_3$-$C_{12}$ carbocycle.

The term "Carbocycle" or "carbocyclic ring", or variants thereof, as used herein are intended to include any stable monocyclic, bicyclic, or tricyclic saturated ring having the specified number of carbons. For example, a $C_3$-$C_{12}$ carbocycle is intended to include a monocyclic, bicyclic, or tricyclic ring having 3, 4, 5, 6, 7, 8, 9, 10, 11, or 12 carbon atoms. Examples of carbocycles include, but are not limited to, cyclopropyl, cyclobutyl, cyclopentyl, cyclohexyl, cycloheptyl, cyclooctyl, and adamantly. Bridged rings are also included in the definition of carbocycle, including, for example, [2.2.1]bicycloheptyl, [3.3.0] bicyclooctane, [4.3.0] bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted (for some embodiments) that a bridge always converts a monocyclic ring into a tricyclic ring.

In one embodiment, the carbocycle is a bridged carbocycle. In a further embodiment, the bridged carbocycle is

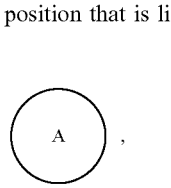

In a further embodiment, each L is independently

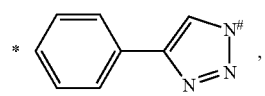

wherein * denotes the position that is linked to

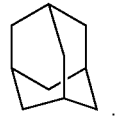

and each $R_L$ is independently a 5- or 6-membered heteroaryl comprising 1 to 3 heteroatoms selected from the group consisting of N, O, and S and is linked to R. In a further embodiment, the heteroaryl is selected from the group consisting of pyrrole, furan, thiophene, thiazole, isothiazole, imidazole, triazole, tetrazole, pyrazole, oxazole, isoxazole, pyridine, pyrazine, pyridazine, and pyrimidine. In a further embodiment, each L is

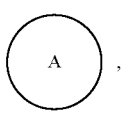

wherein * denotes the position that is linked to

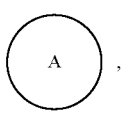

and # denotes the position that is linked to R. In a further embodiment, each R is independently

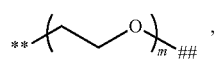

wherein each m is independently 1, 2, 3, 4, 5, 6, 7, 8, 9, 10, 11, 12, 13, 14, 15, 16, 17, 18, 19, 20, 21, 22, 23, or 24; ** denotes the position that is linked to L; and ## denotes the position that is linked to T. In a further embodiment, each m is independently 12, 13, 14, 15, 16, 17, or 18. In a further embodiment, each R is
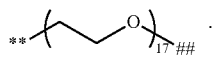
In one embodiment, the compound is
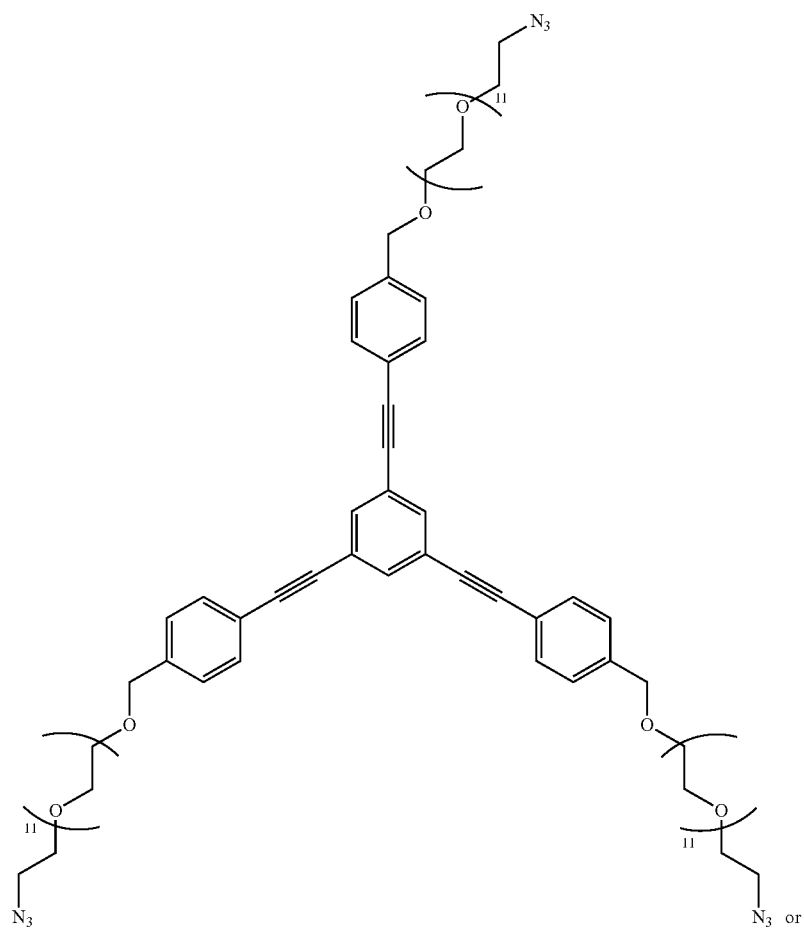

-continued

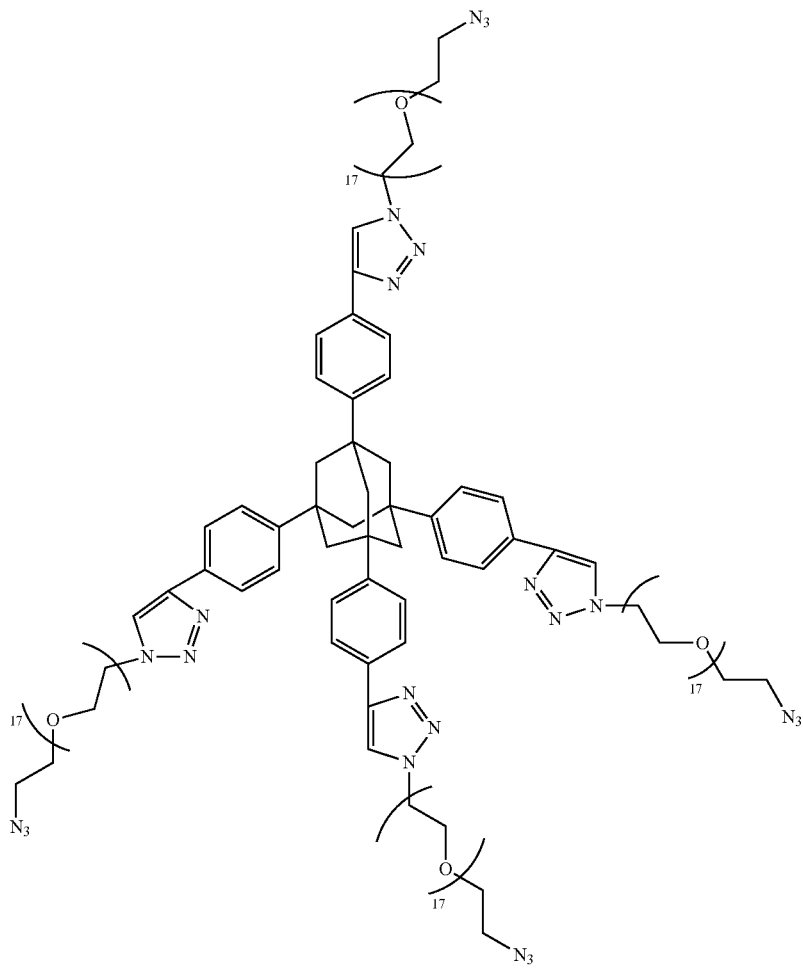

Embodiments of the present disclosure are directed to multiple arm linker molecules (i.e., "linker" or in the plural form, "linkers"), and in particular, according to some embodiments, a three-arm linker molecule, configured for attachment to a plurality of affinity molecules for recognition of, for example, multiple protein biomarkers in identification and/or sensor systems, devices and methods. In some embodiments, the linker may be utilized for multiplex recognition imaging by Atomic Force Microscopy (AFM). Embodiments of the linker may be used as a chemical mimic of bi-specific antibodies for targeting and drug delivery. Embodiments of the linker used as a chemical scaffold for peptide aptamers and peptides conjugated to this scaffold display higher affinity than unconjugated peptides. Some embodiments of the present disclosure are also directed to a four-arm linker, which may be used to attach, for example, three different affinity molecules. Some embodiments are directed at methods for synthesizing the linker(s) described herein.

Example experimental details and results are as follows.

EXPERIMENTAL INFORMATION

Scheme:

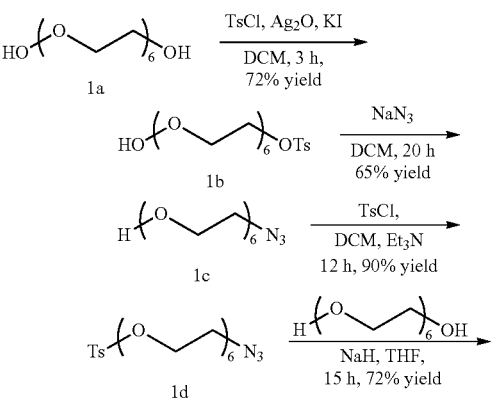

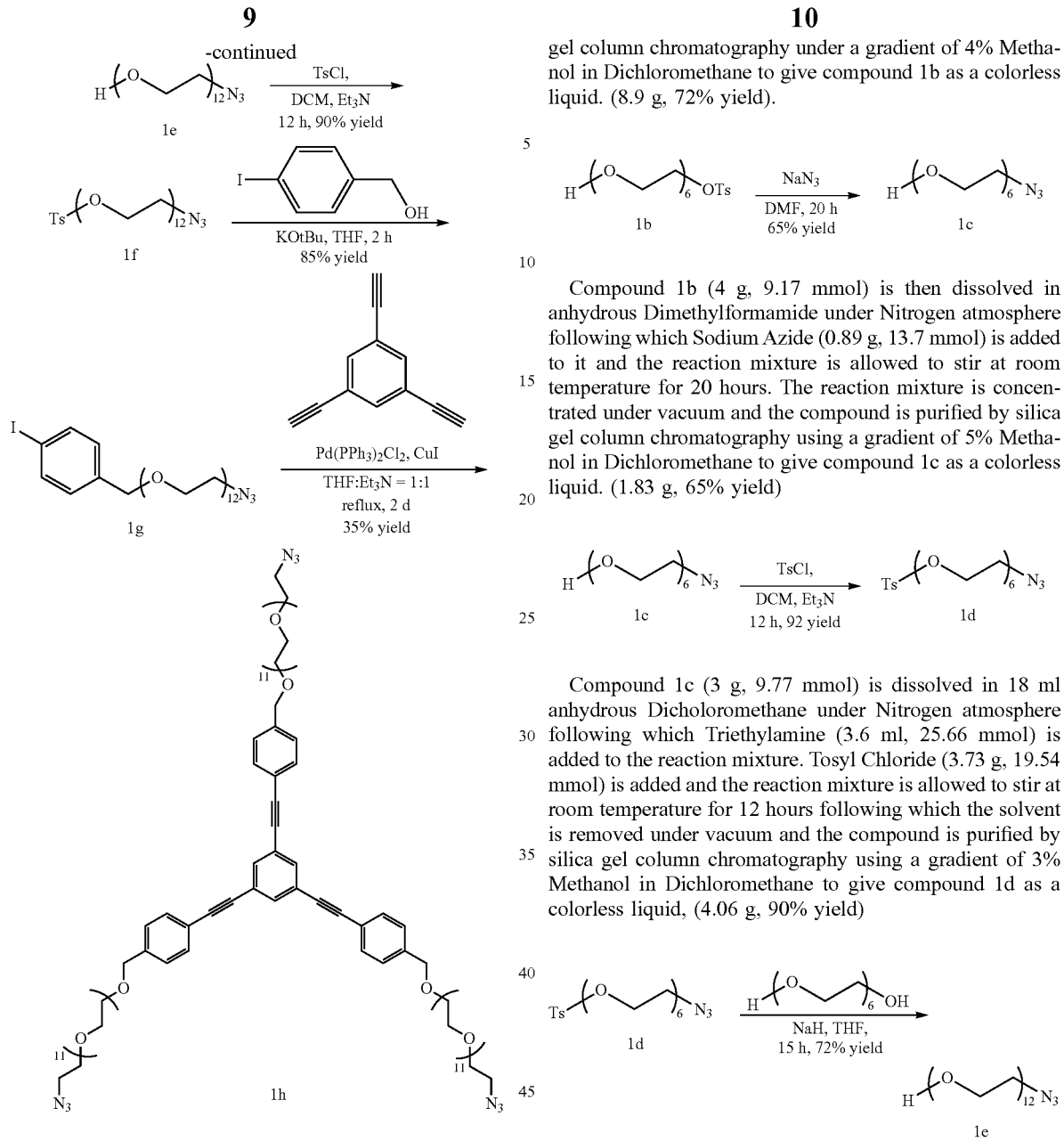

Example Synthesis

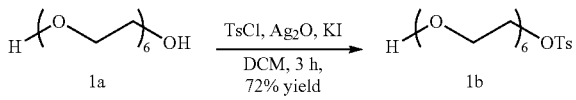

Hexaethyleneglycol (8 g, 28.37 mmol) is dissolved in anhydrous Dichloromethane in Nitrogen atmosphere and the mixture is cooled to 0° C., following which Silver Oxide (6.57 g, 28.37 mmol) and Potassium Iodide (2.35 g, 14.19 mmol) are added to the reaction mixture. Tosyl Chloride (5.95 g, 31.21 mmol) is added and the reaction mixture is allowed to stir at 0° C. for 3 hours. After completion, Ag$_2$O is filtered off and the solvent is evaporated under vacuum and product is purified by column purification using silica gel column chromatography under a gradient of 4% Methanol in Dichloromethane to give compound 1b as a colorless liquid. (8.9 g, 72% yield).

Compound 1b (4 g, 9.17 mmol) is then dissolved in anhydrous Dimethylformamide under Nitrogen atmosphere following which Sodium Azide (0.89 g, 13.7 mmol) is added to it and the reaction mixture is allowed to stir at room temperature for 20 hours. The reaction mixture is concentrated under vacuum and the compound is purified by silica gel column chromatography using a gradient of 5% Methanol in Dichloromethane to give compound 1c as a colorless liquid. (1.83 g, 65% yield)

Compound 1c (3 g, 9.77 mmol) is dissolved in 18 ml anhydrous Dicholoromethane under Nitrogen atmosphere following which Triethylamine (3.6 ml, 25.66 mmol) is added to the reaction mixture. Tosyl Chloride (3.73 g, 19.54 mmol) is added and the reaction mixture is allowed to stir at room temperature for 12 hours following which the solvent is removed under vacuum and the compound is purified by silica gel column chromatography using a gradient of 3% Methanol in Dichloromethane to give compound 1d as a colorless liquid, (4.06 g, 90% yield)

To a solution of Polyethyleneglycol (5.5 g, 19.5 mmol) in 20 ml anhydrous Tetrahydrofuran under Nitrogen atmosphere at 0° C., Sodium Hydride is added and stirred until the evolution of Hydrogen ceases. Then, compound 1d (3 g, 6.5 mmol), dissolved in 15 ml anhydrous Tetrahydrofuran, is added to the reaction mixture. Then, the reaction mixture is allowed to come to room temperature and stirred for 15 hours under Nitrogen atmosphere when 1 d gets consumed. The reaction is quenched by adding 2 ml Methanol after cooling in an ice bath. The reaction mixture is concentrated under vacuum and is purified by silica gel column chromatography in a gradient of 4% Methanol in Dichloromethane to obtain compound 1eas a colorless liquid. (2.67 g, 72% yield)

$^1$H NMR (400 MHz, CDCl$_3$): 2.686 (s, 1H); 3.34 (t, 2H, J=8 Hz); 3.552-3.777 (m, 46H): $^{13}$C NMR (100 MHz, CDCl$_3$): δ=72.533, 70.652-69.995, 61.558, 50.642; HRMS: Expected mass: 571.33; Obtained mass: 572.33 (M+H)

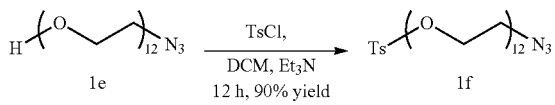

Compound 1e (2.5 g, 4.38 mmol) is dissolved in 15 ml anhydrous Dicholoromethane under Nitrogen atmosphere following which Triethylamine (3 ml, 21.53 mmol) is added to the reaction mixture. Tosyl Chloride (1.67 g, 8.76 mmol) is added and the reaction mixture is allowed to stir at room temperature for 12 hours, following which the solvent is removed under vacuum and the compound is purified by silica gel column chromatography using a gradient of 3.5% Methanol in Dichloromethane to give compound if as a colorless liquid. (2.86 g, 90% yield)

$^1$H NMR (400 MHz, CDCl$_3$): 2.97 (s, 3H); 3.37 (t, 2H, J=5.2 Hz); 3.575-3.3.689 (m, 44H); 4.505 (t, 2H, J=4.8 Hz); 7.35 (d, 2H, J=8 Hz); 7.79 (d, 2H, J=8 Hz); $^{13}$C NMR (100 MHz, CDCl$_3$): δ=144.71, 132.920, 129.756, 127.851, 70.605-70.404, 69.920, 69.206, 68.543, 50.568, 21.539, HRMS: Expected mass: 725.23; Obtained mass: 726.33 (M+H).

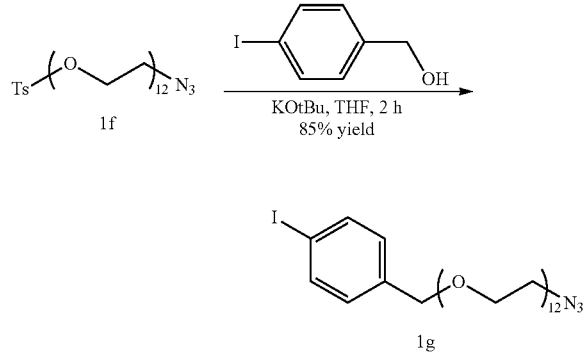

To a solution of if (2 g, 2.76 mmol) in 4 ml anhydrous Tetrahydrofuran under Nitrogen atmosphere, p-Iodobenzylalcohol (0.84 g, 3.59 mmol) is added followed by the addition of Potassium-tert-butoxide (482.5 g, 4.3 mmol) and the reaction is stirred for two hours at room temperature, following which the reaction is quenched by adding 2 ml Methanol after cooling it down to 0° C. in an ice bath. The compound is purified using a gradient of 3.5% Methanol in Dichloromethane to obtain compound 1g as a yellowish oil. (1.85 g, 85% yield)

$^1$H NMR (400 MHz, CDCl$_3$): 3.301 (t, 2H, J=5.2 Hz); 3.565-3.582 (m, 46H); 4.423 (s, 2H); 7.02 (d, 2H, J=8 Hz); 7.57 (d, 2H, J=8.4 Hz); $^{13}$C NMR (100 MHz, CDCl$_3$): δ=138.004, 137.259, 129.451, 92.838, 72.317, 70.538-70.404, 69.905, 69.496, 50.538; MALDI-MS: Expected mass: 787.68; Obtained mass: 788.84 (M+H), 810.58 (M+Na), 826.55 (M+K).

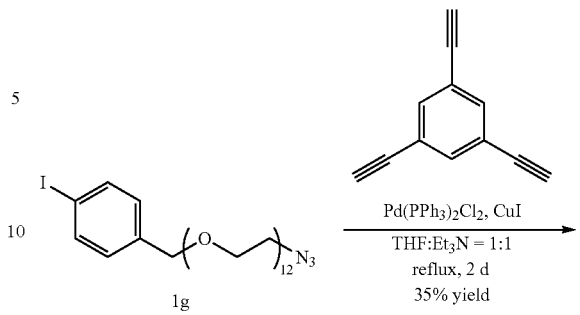

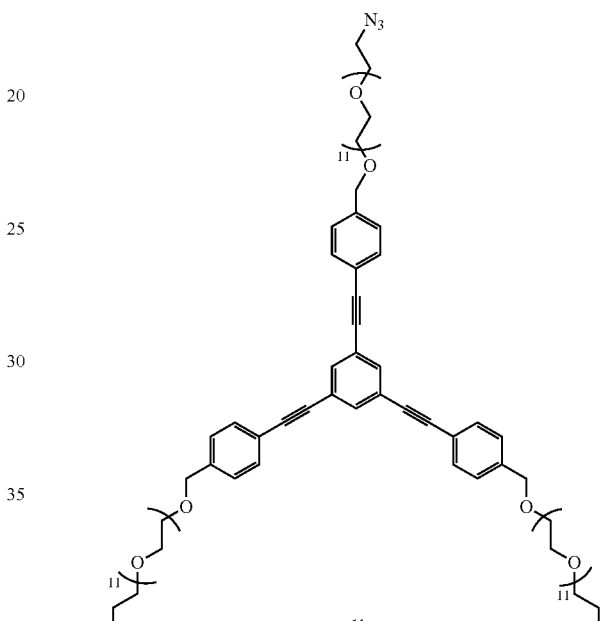

Compound 1g (1 g, 1.27 mmol) is dissolved in 7.5 ml anhydrous Tetrahydrofuran followed by the addition of 7.5 ml of Triethylamine under Nitrogen atmosphere. Then 1,3,5-Triethynylbenzene (0.062 g, 0.412 mmol) is added to the reaction mixture and then the solvent is degassed by passing Nitrogen through the reaction mixture. This is followed by the addition of bis(triphenylphosphine)Palladium(II)dichloride (14.4 mg, 0.02 mmol, 5 mol %) and Copper(I)Iodide (3.9 mg, 0.02 mmol, 5 mol %) and the reaction mixture is set to reflux at 70° C. for 48 hours following which the catalyst is filtered off and the solvent is evaporated under vacuum and the compound is purified by silica gel column chromatography under a gradient of 4% Methanol in Dichloromethane to obtain compound 1h as a yellowish oil. (306.86 g, 35% yield)

$^1$H NMR (400 MHz, CDCl$_3$): 3362 (t, 6H, J=5.2 Hz); 3.619 3.675 (m, 138H); 4.567 (s, 1H); 7.326 (d, 6H, J=8.4 Hz); 7.485 (d, 6H, J=8 Hz); 7.623 (s, 3H); $^{13}$C NMR (100 MHz, CDCl$_3$): δ=139.031, 133.969, 131.684, 127.576, 124.018, 121.904, 90.426, 87.754, 72.786, 70.679-70.545, 70.010, 69.660, 50.665. MALDI-MS: Expected mass: 2128.14, obtained mass: 2151.75 (M+Na), 2167.65 (M+K).

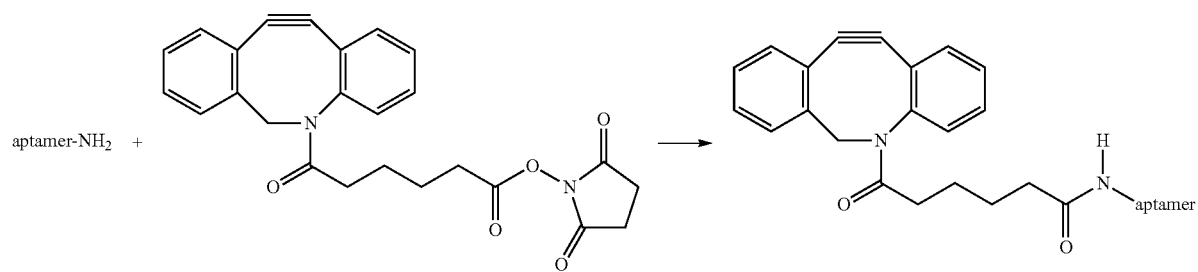
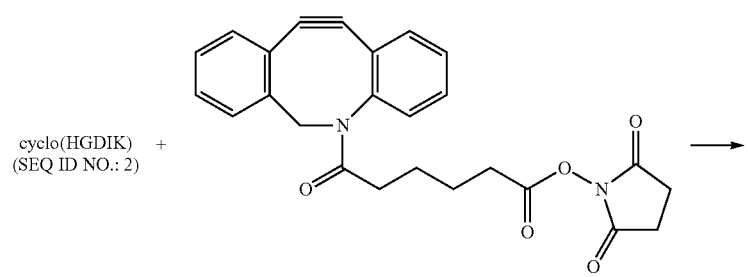
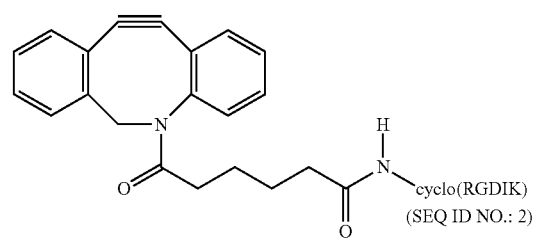
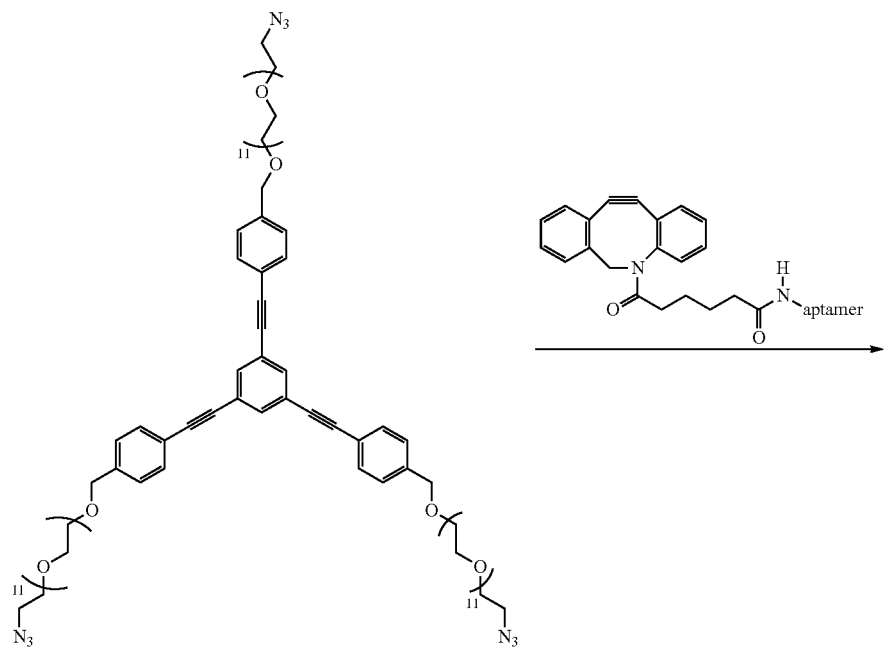

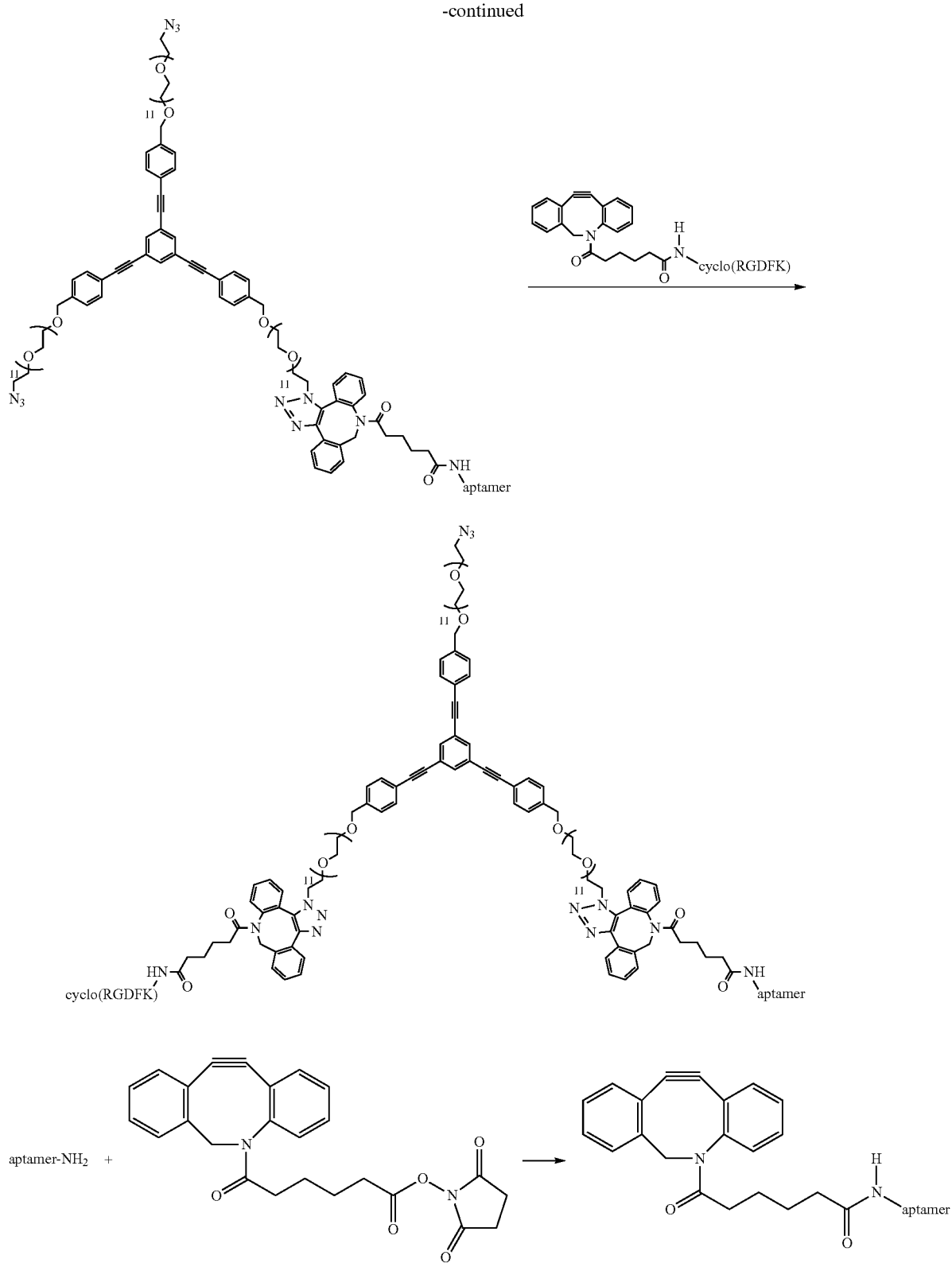

10 μL of Anti-thrombin aptamer 5'-/5AmMC12/GGTTG-GTGTGGTTGG-3' (SEQ ID NO.: 1) of 1 mM concentration dissolved in D.I. water is taken and mixed with 30 μL pH 8.5 Phosphate buffer. DBCO-NHS ester (05 mg, 0.0011 mmol) is dissolved in 80 μL DMSO to prepare a 15 mM solution of DABCO-NHS in DMSO. 40 μL of the ester is mixed with the aptamer solution and stirred for 30 mins at room temperature following which another 40 μL portion is added to the reaction mixture and the reaction mixture is stirred for 1.5 hours more. The reaction mixture is purified by reverse phase HPLC using a C18 column and characterized by MALDI-MS. MALDI-MS: expected 5305.77, obtained 5295.12 cyclo(RGDIK) (SEQ ID NO.: 2) +

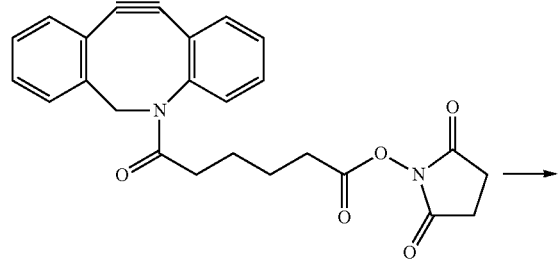

→

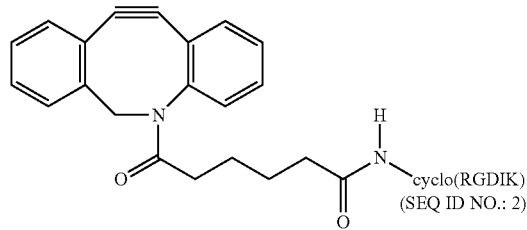
cyclo(RGDIK) (SEQ ID NO.: 2)

10 μL of cyclo(RGDFK) (SEQ ID NO.: 2) peptide of 1 mM concentration dissolved in D.I. water is taken and mixed with 30 μL pH 8.5 Phosphate buffer. DBCO-NHS ester (80 μL, 15 (mM)) is prepared as stated above. 40 μL of the ester is mixed with the peptide solution and stirred for 30 mins at room temperature following which another 40 μL portion is added to the reaction mixture and the reaction mixture is stirred for 1 hr or more. The reaction mixture is purified by reverse phase HPLC using a C18 column and characterized by MALDI-MS. MALDI-MS: expected 920.052, obtained: 919.352.

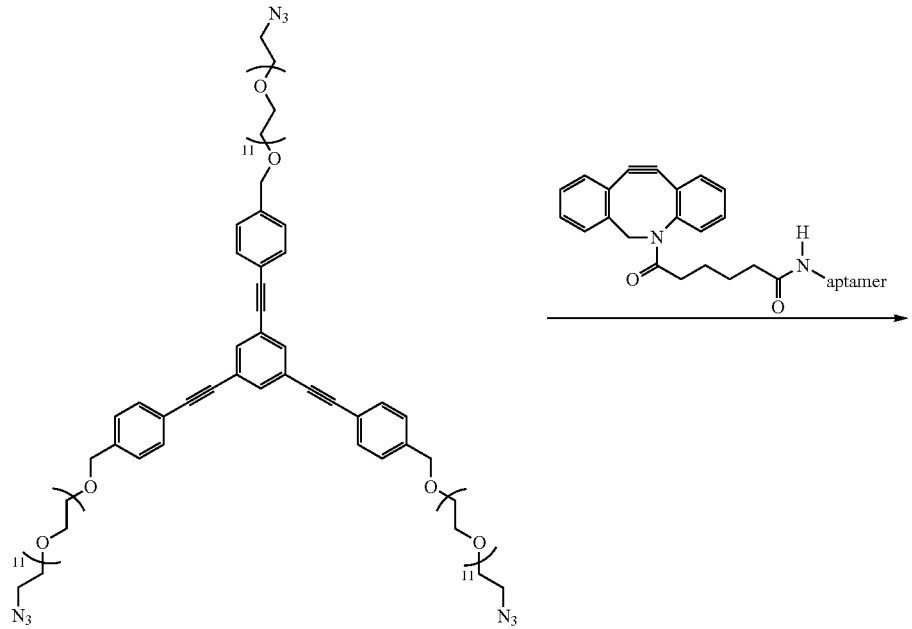

-continued
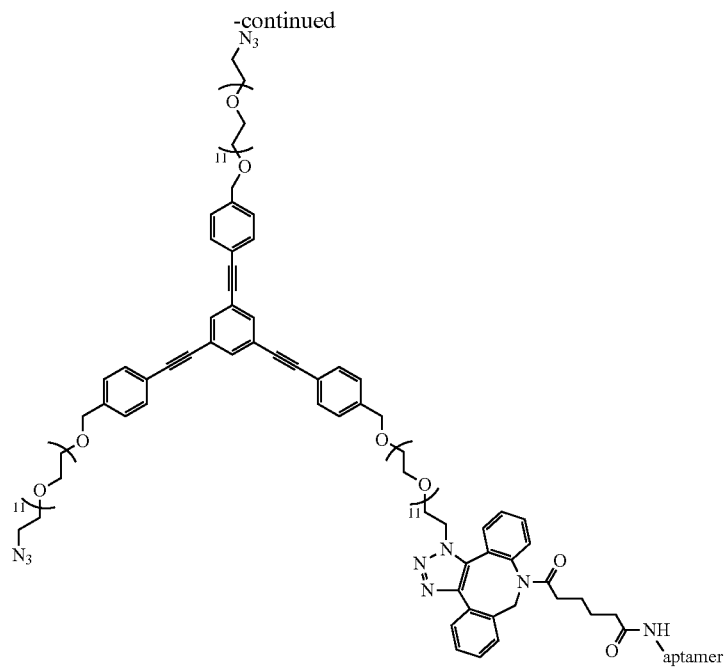
Excess of compound 1h (1 mg, 0.0004 mmol) is added to a solution of DBCO functionalized aptamer (30 µL, 200 (µM)) in pH 7 TEAA buffer (50 mM) and allowed to stir at room temperature for 4 hours following which it is purified employing RP-HPLC using a C18 column and characterized by MALDI-MS. (expected 7424.59, obtained 7424.15)
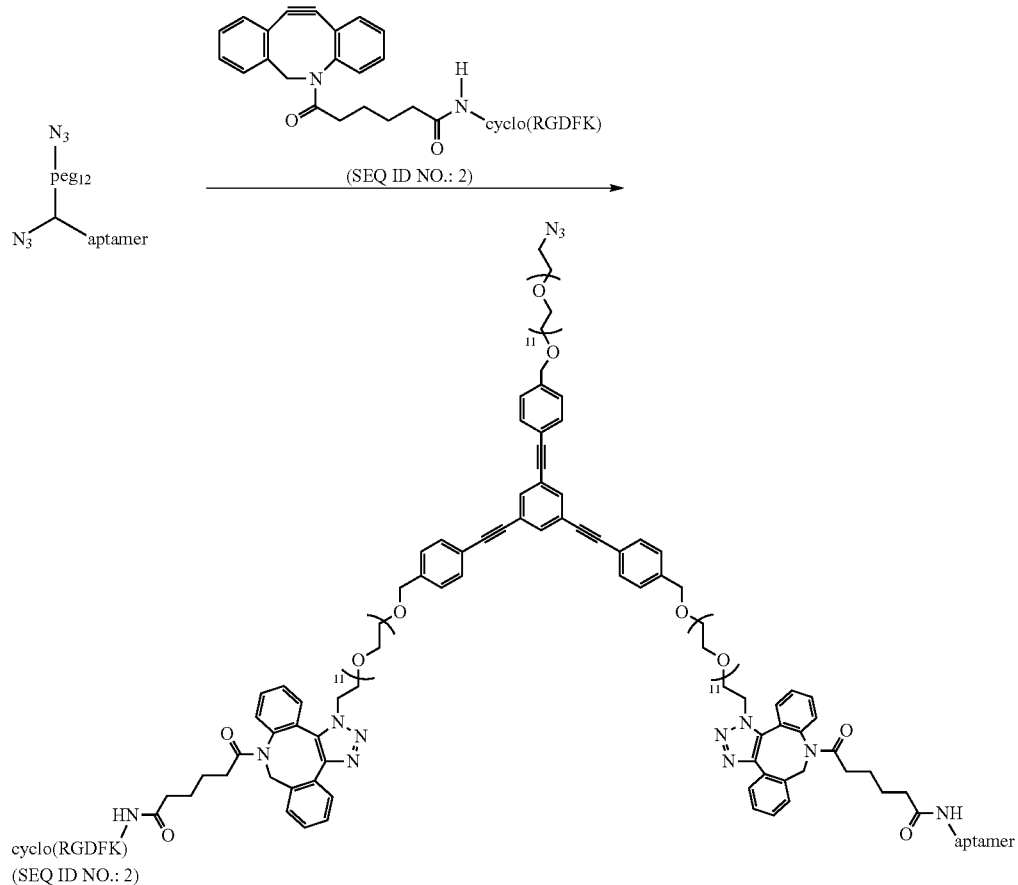

15 μL DNA functionalized Linker (100 (μM)) is mixed with 15 μL DBCO functionalized RGD (150 (μM)) and the reaction is stirred at room temperature for 15 mins. following which it is purified by RP-HPLC using a $C_{18}$ column and characterized by MALDI-MS (expected: 8343.94, obtained: 8343.91).

Example: Synthesis of Multiple Aptamer-3 Arm Linker Conjugate

Scheme:

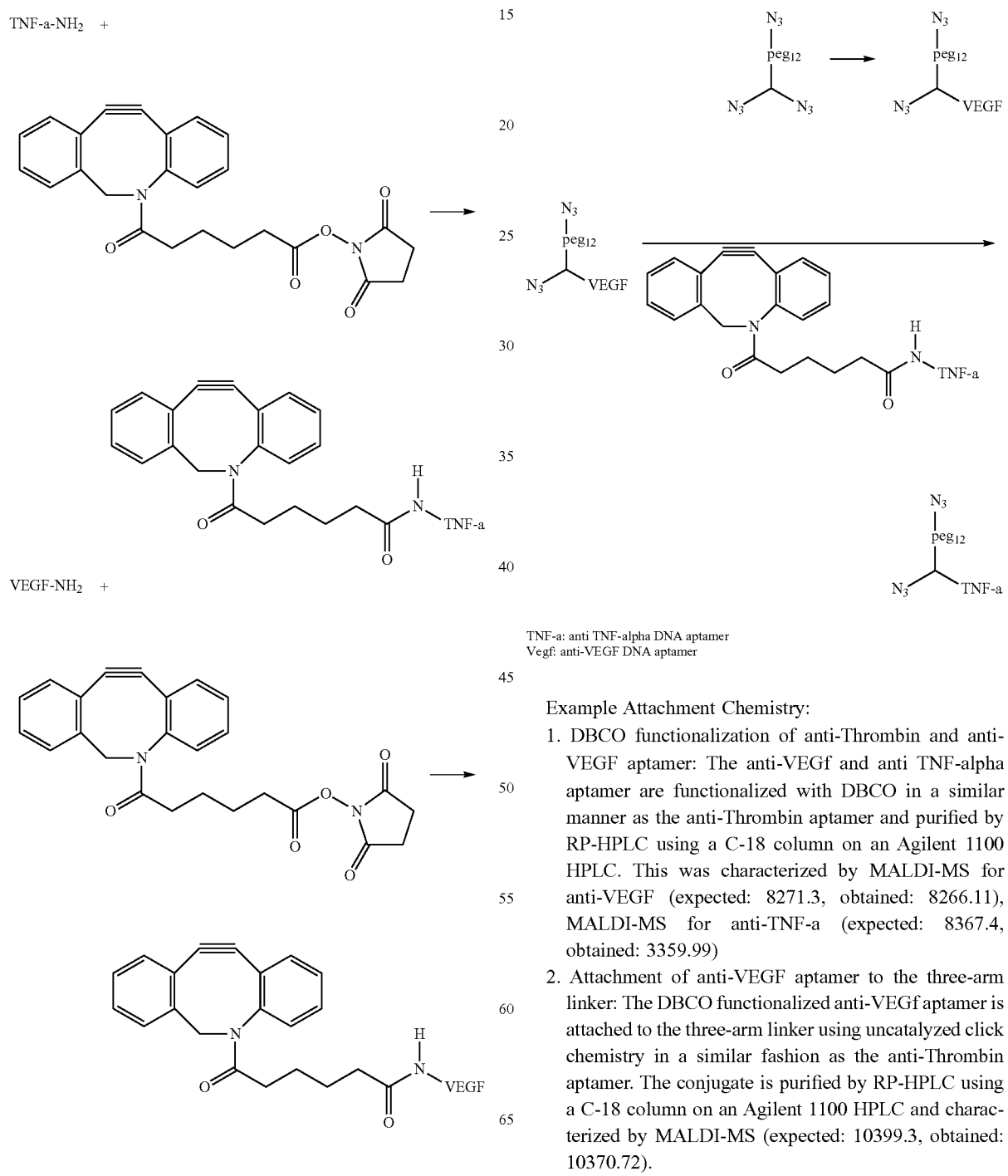

TNF-a: anti TNF-alpha DNA aptamer
Vegf: anti-VEGF DNA aptamer

Example Attachment Chemistry:
1. DBCO functionalization of anti-Thrombin and anti-VEGF aptamer: The anti-VEGf and anti TNF-alpha aptamer are functionalized with DBCO in a similar manner as the anti-Thrombin aptamer and purified by RP-HPLC using a C-18 column on an Agilent 1100 HPLC. This was characterized by MALDI-MS for anti-VEGF (expected: 8271.3, obtained: 8266.11), MALDI-MS for anti-TNF-a (expected: 8367.4, obtained: 3359.99)
2. Attachment of anti-VEGF aptamer to the three-arm linker: The DBCO functionalized anti-VEGf aptamer is attached to the three-arm linker using uncatalyzed click chemistry in a similar fashion as the anti-Thrombin aptamer. The conjugate is purified by RP-HPLC using a C-18 column on an Agilent 1100 HPLC and characterized by MALDI-MS (expected: 10399.3, obtained: 10370.72).

3. Attachment of anti TNF-alpha aptamer: 1.5 equivalents of DBCO functionalized TNF-alpha aptamer is reacted with one equivalent of three arm linker functionalized anti VEGF-aptamer in presence of $MgCl_2$ (200 (mM)). The reaction mixture is kept at room temperature tor 5 mins following which it is purified by RP-HPLC using a C18 column on an Agilent 1100 HPLC to obtain the three arm linker conjugated with two aptamers.

The attachment chemistry with aptamer and the three-arm linker using $Mg^{2+}$ has been verified, with respect to some embodiments, by attaching an anti-thrombin aptamer and a random 24-mer DNA to the three-arm linker. The conjugate had been purified by RP-HPLC and characterized by MALDI-MS. In some embodiments, the $Mg^{2+}$ has been found to assist the reaction rate.

Recognition Imaging. Recognition imaging was performed with anti-Thrombin aptamer and RGD functionalized three arm tinker attached to AFM tips in AC (MAC) mode operation on an Agilent 5500 AFM. Silicon tips from Nanoworld were used having a length of 125 μm, width 35 μm and thickness 800 nm with force constant value of 0.14 N/m. Backsides of these tips were coated with 1 nm Ti/40 nm Ni. A solution containing a mixture of Thrombin and Integrin was used with a concentration of 0.02 ng/ul of each protein. Recognition experiments were performed on AFM and further selective blocking of each protein was done to verify the specificity of recognition. The images obtained are shown in FIG. 1.

The recognition images show that the linker can be used for multiple recognition imaging on AFM, and thus, may be used in detecting specific proteins in a complex mixture (for example). Also, the linker can potentially be applied as a chemical mimic of bi-specific antibodies and may be used for targeting and drug delivery purposes. Such embodiments of the linker are robust in that a desired number of biomolecules or drug candidates can be attached on it specifically.

Synthesis of Cyclic Peptide Using Three-Arm Linker as the Scaffold

Example Experimental Results:

The three-arm linker was used, for example, as a scaffold for peptides. Peptides cyclized using the three-arm linker scaffold show a higher force of binding to the cognate protein than a free peptide attached to a linear PEG linker. A fibronectin mimetic peptide aptamer targeting alpha5beta1 was used. The cyclized peptide shows a higher force of binding compared to the linear one as concluded by force measurement using AFM. This shows that the three-arm linker may be used as a chemical scaffold, for example, for peptide aptamers to increase their affinity to their cognate proteins.

In some embodiments, the structure of the peptide aptamer is:

(SEQ ID NO.: 3)

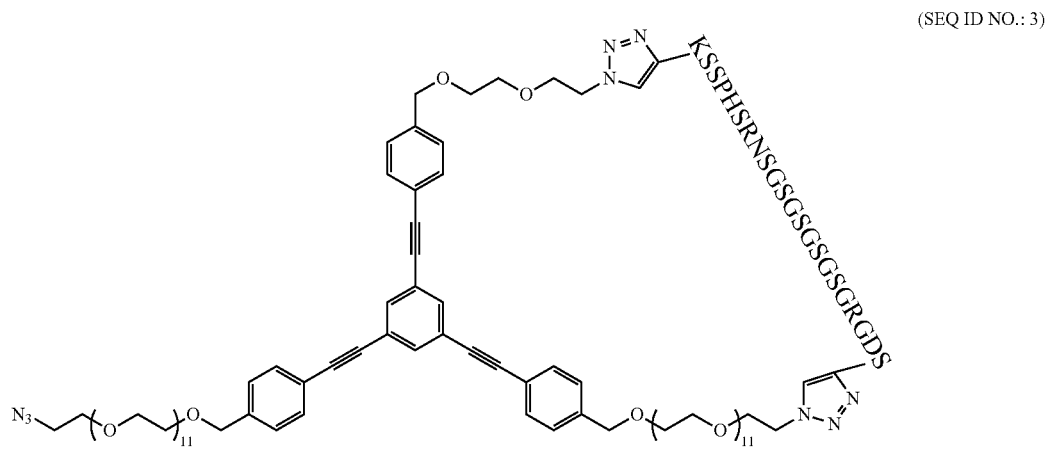

A linear linker peg linker was used, functionalized with the peptide as a control.
2. Example Synthesis of Linear Peptide:
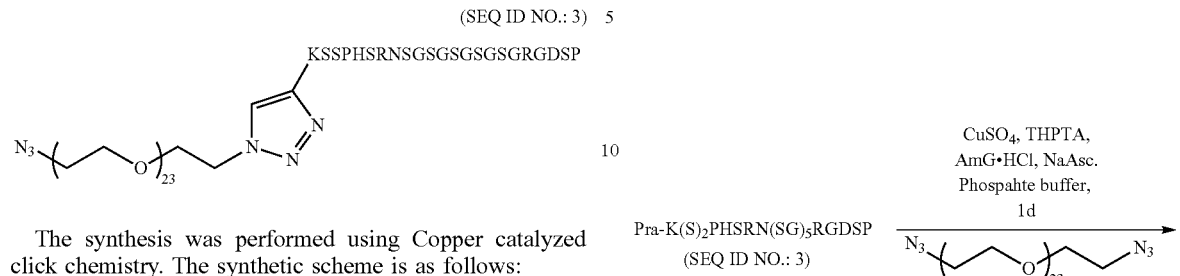
The synthesis was performed using Copper catalyzed click chemistry. The synthetic scheme is as follows:
1. Example Synthesis of Cyclic Peptide Based on Three-Arm Linker Scaffold:
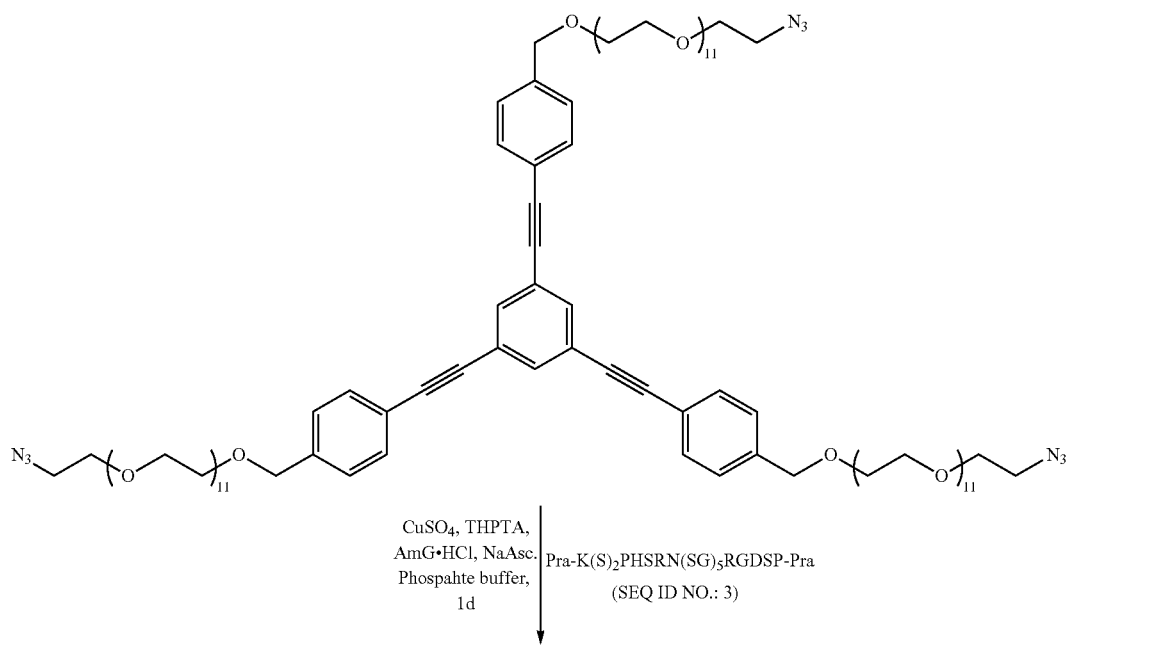
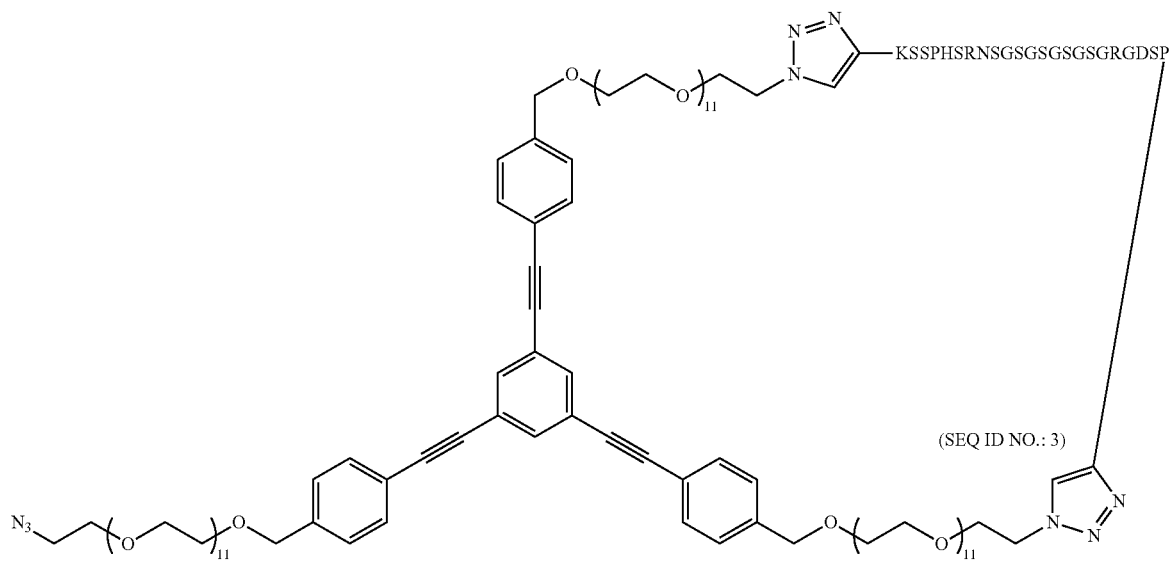

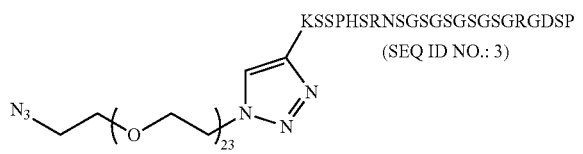

KSSPHSRNSGSGSGSGSGRGDSP
(SEQ ID NO.: 3)

Experimental Details

Example Synthesis of the Cyclic Peptide:

A fibronectin mimetic peptide functionalized with propargylglycine at both ends' was used for the conjugation reaction. The synthesis was preformed followed previously reported reaction protocol[2]. To 5 ul of the peptide (4 mM) functionalized with prpargylglycine a in D.I. water is added 81.5 ul of 100 mM Phosphate buffer (pH 7) followed by the addition of 2 ul of the three arm linker (10 mM) following which is added 1.5 ul a premixed solution of $CuSO_4$ (0.1 mM) and THPTA ligand (0.5 mM). 5 ul AminoGuanidine Hydrochloride (5 mM) was added to the reaction mixture followed by the addition of 5 ul Sodium Ascorbate (5 mM). All the solutions were properly degassed with Argon and the reaction mixture is allowed to stir for 1 day at room temperature following which Copper was removed by dialysis and the reaction mixture was purified by RP-HPLC using a Zorbax eclipse C-18 column. The compound was characterized by MALDI-MS. (expected: 4463.3, obtained: 4465.08). HPLC analysis showed the ratio of the cyclized peptide to uncyclized peptide was 35:65. The compound was characterized by reacting it with 2-(cyclooct 2 yn-1-yloxy) acetic acid. The cyclized peptide added only one 2-(cyclooct-2-yn 1-yloxy)acetic acid while the uncyclized peptide added two of 2-(cyclooct-2-yn-1-yloxy)acetic acid.

Example Synthesis of Linear 24-Peg Di-Azide Linker:

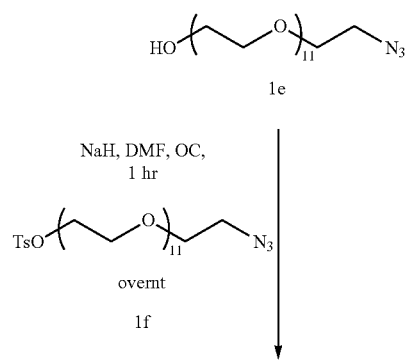

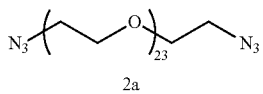

Compound 1e (1 g, 1.7 mmol) was dissolved in anhydrous DMF (5 ml) in an ice bath followed by the addition of Sodium Hydride (53 mg, 2.21 mmol, 1.3 eq). The reaction mixture is stirred for 1 hr or until the evolution of Hydrogen ceases following which compound if (1.23 g, 1.7 mmol) was dissolved in 5 ml anhydrous DMF and added to the reaction mixture. The reaction mixture was stirred for 15 hrs at room temperature following which it was quenched by adding a few drops of methanol after cooling it in an ice bath. After that the solvent was evaporated under vacuum and the compound was purified by silica-gel column chromatography under a gradient of 4% Methanol in Dichloromethane to obtain a colorless liquid (1.34 g, 70% yield). $^1$H NMR (400 MHz, $CDCl_3$): 3.353 (t, 4H, J=4.8 Hz); 3.608-3.655 (m, 92H). $^{13}$C NMR (100 MHz, $CDCl_3$): δ=70.605-70.002, 50.65, MALDI-MS: Expected mass: 1124.65; Obtained mass: 1147.55 (M+Na), 1163.50 (M+K)

Example Synthesis of Linear Peptide:

The same fibronectin mimetic peptide was used to prepare the linear control peptide. This peptide had one Propargylglycine modification at it's N-terminus. The synthesis was similar to the cyclic peptide. However the reaction was completed within 1 hr. at room temperature. The compound was purified by RP-HPLC and characterized by MALDI-MS. (expected: 3364.85, obtained: 3362.20).

Figure 2A:
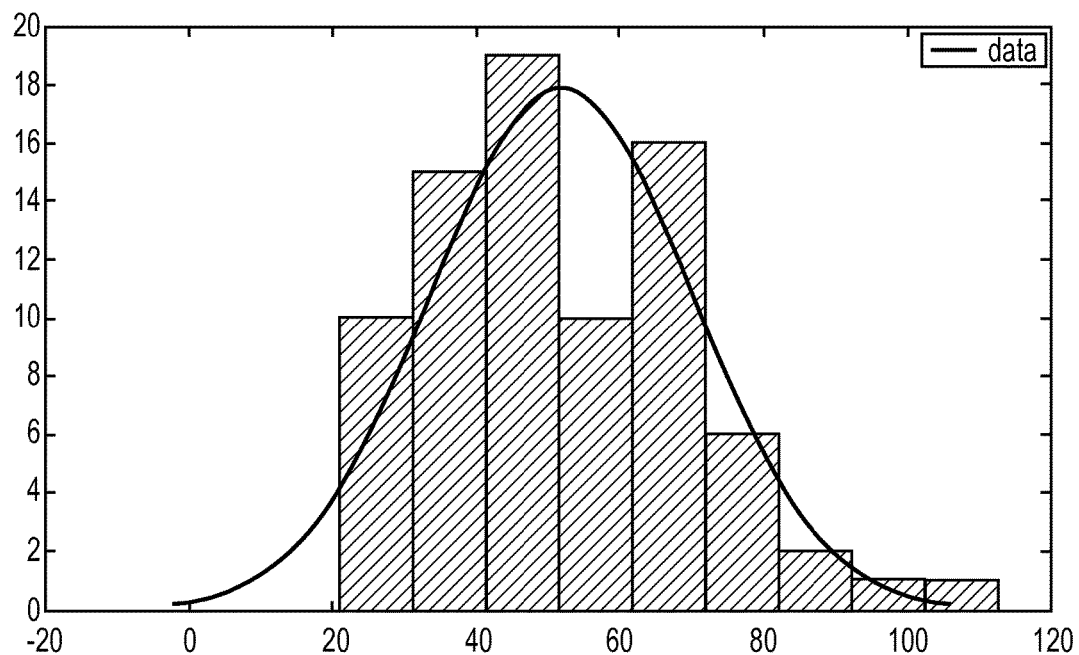
FIGS. 2A, 2B: Force histogram for cyclic peptide at a loading rate of 30 nN/s, mean force: 51.87 pN (FIG. 2A) and Force histogram for linear peptide at a loading rate of 30 nN/s, mean force: 40.71 pN (FIG. 2B).
Figure 2B:
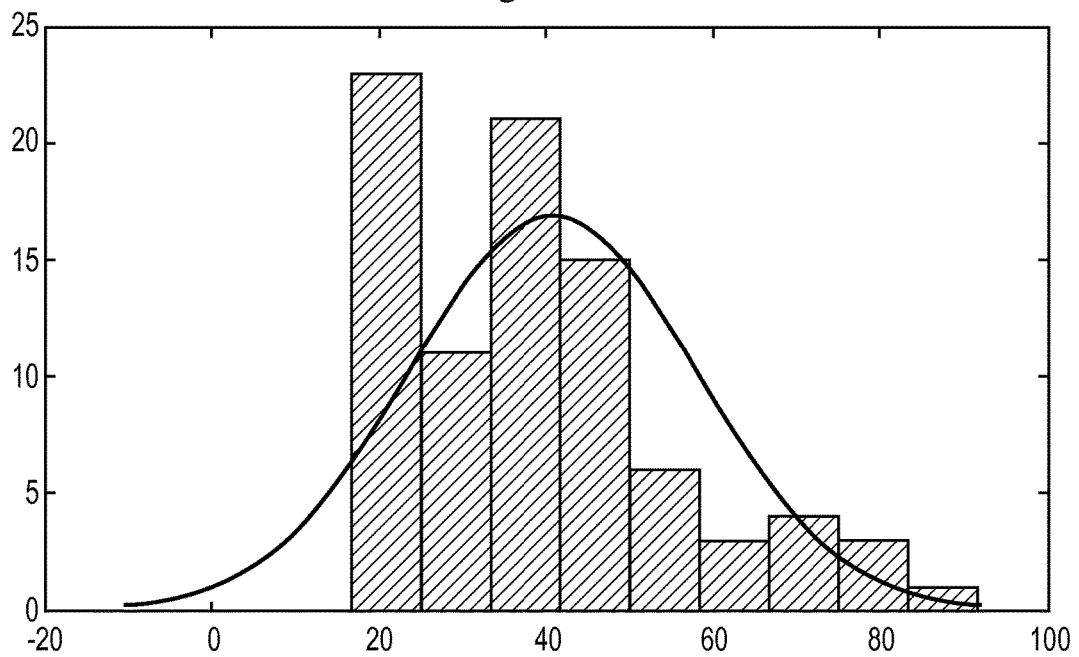

Force Spectroscopy:

Force measurements were done using the cyclic peptide and the linear control peptide at loading rates on 10 nN/s, 15 nN/s, 20 nN/s, 25 nN/s, 30 nN/s on an Agilent 5500 AFM. SiN probes from Veecoprobes having force constant 0.05 N/m were used fix Force measurement. Tips were functionalized using a protocol developed in our lab.[3] A 10 ng/ul solution of integrin was immobilized on mica using glutaraldehyde and force measurements were carried out in 1×PBS buffer pH 7.4 containing 1 mM $MgCl_2$. The cyclized peptide, in some embodiments, consistently displays a higher force of unbinding compared to its linear counterpart. Force histogram obtained for a loading rate 30 nN/s for the cyclic and the linear peptide is shown in FIG. 2.

4-Arm Linker:

A 4 arm linker is configured to be attached with three different aptamers and may potentially be applied for multiple recognition, recognition imaging, targeting and drug delivery. The structure of the 4 arm linker is as follows:

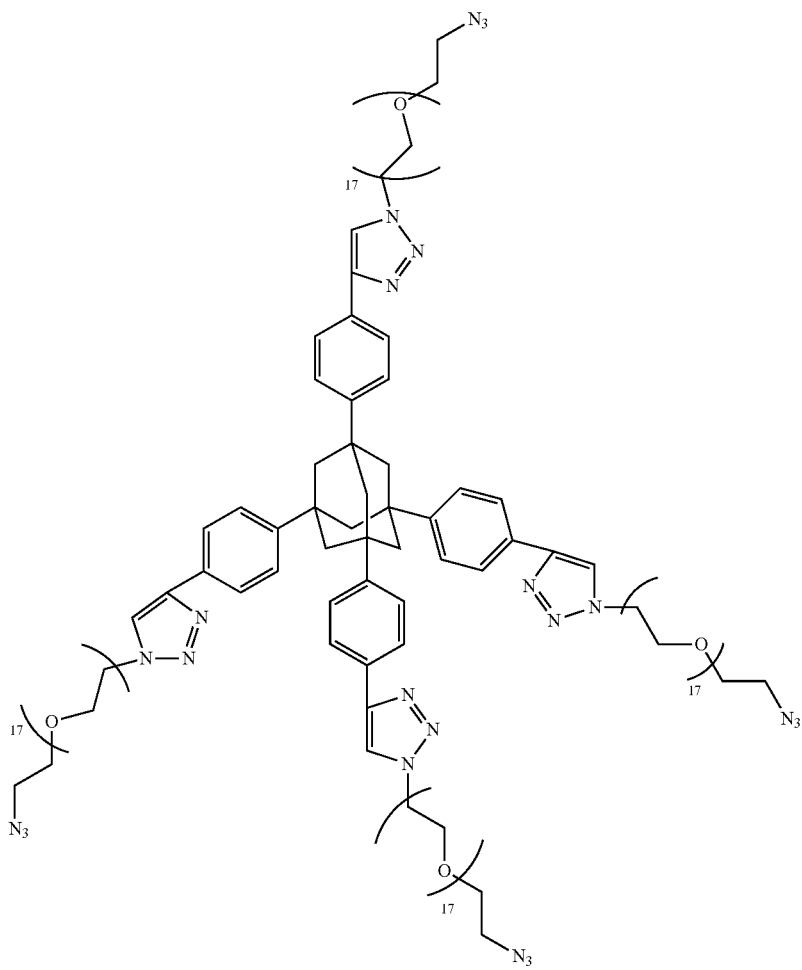

Any and all references to publications or other documents, including but not limited to, patents, patent applications, articles, webpages, books, etc., presented in the present application are herein incorporated by reference in their entirety.

Embodiments described herein are for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents.

REFERENCES

1. Craig et al. *Langmuir* 2008, 24, 10282-10292.
2. Hong et al. *Angew. Chem. Intl. Edn.* 2009, 48, 9879-9883.
3. Senapati et al. *Langmuir* 2013, 29, 14622-14630.

What is currently claimed:

1. A compound of the following formula:

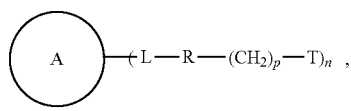

wherein:

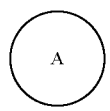

is phenyl with a plurality of available attachment points;
each p is independently 0, 1, or 2; and n is 3, 4, 5, 6, 7, 8, or 9
each L is independently a

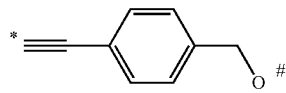

wherein * denotes the position that is linked to

, and wherein # denotes the position that is linked to R; wherein each R is independently

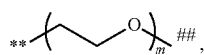, wherein each m is independently 1, 2, 3, 4, 5, 6, 7, 8, 9, 10, 11, 12, 13, 14, 15, 16, 17, 18, 19, 20, 21, 22, 23, or 24; ** denotes the position that is linked to L; and ## denotes the position that is linked to T; wherein T is a reactive group.

2. The compound of claim 1, wherein each m is independently 6, 7, 8, 9, 10, 11, or 12.

3. The compound of claim 1, wherein each T is independently a reactive group selected from the group consisting of $ONH_2$, SH, $NH_2$, alkyne, alkene, vinyl sulfone, maleimide, carboxylic acids, aldehyde, ketone, and, $N_3$.

4. A compound of the following formula:

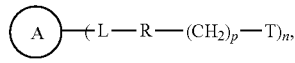

wherein:

is phenyl with a plurality of available attachment points;
each p is independently 0, 1, or 2; and n is 3, 4, 5, 6, 7, 8, or 9
each L is independently a

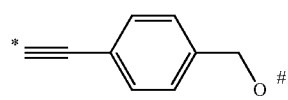

wherein * denotes the position that is linked to

, and wherein # denotes the position that is linked to R; each R is independently
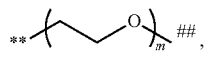
wherein each m is independently 1, 2, 3, 4, 5, 6, 7, 8, 9, 10, 11, 12, 13, 14, 15, 16, 17, 18, 19, 20, 21, 22, 23, or 24; ** denotes the position that is linked to L; and ## denotes the position that is linked to T; and wherein each T is $N_3$.
5. A compound, wherein the compound is
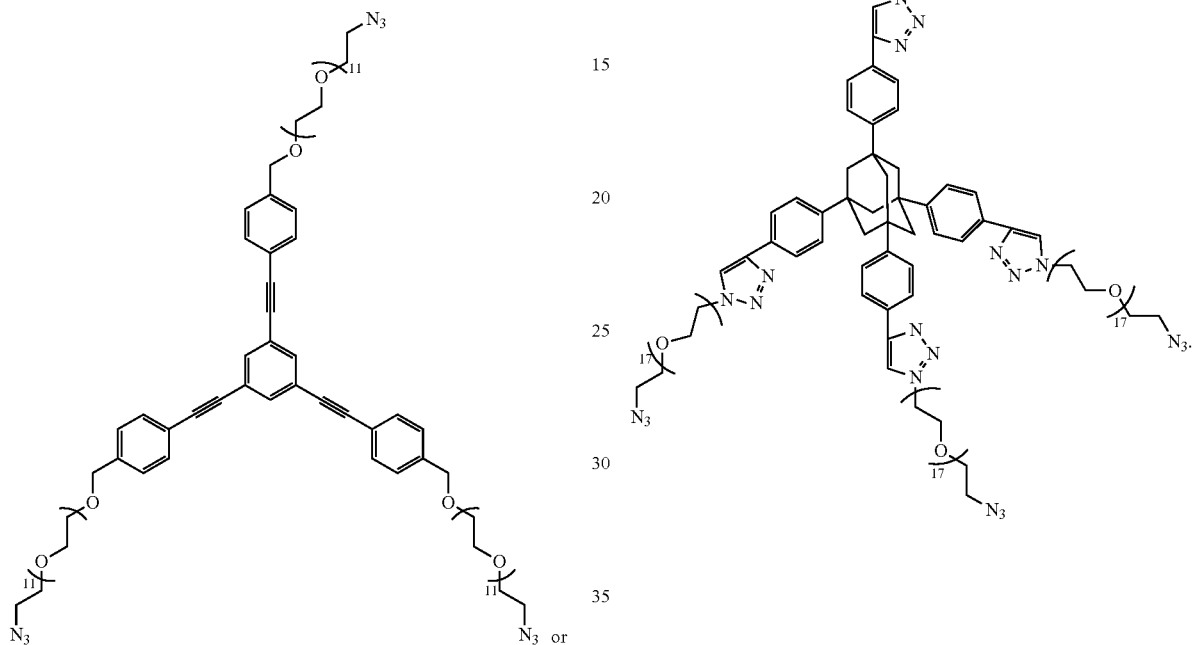
* * * * *